US008884040B2

(12) United States Patent
Krull et al.

(10) Patent No.: US 8,884,040 B2
(45) Date of Patent: Nov. 11, 2014

(54) CONTINUOUS METHOD FOR PRODUCING FATTY ACID AMIDES

(75) Inventors: Matthias Krull, Harxheim (DE); Roman Morschhaeuser, Mainz (DE); Michael Seebach, Hofheim (DE); Ralf Bierbaum, Frankfurt am Main (DE); Joerg Appel, Tueβling (DE)

(73) Assignee: Clariant Finance (BVI) Limited, Tortola (VG)

( * ) Notice: Subject to any disclaimer, the term of this patent is extended or adjusted under 35 U.S.C. 154(b) by 353 days.

(21) Appl. No.: 12/935,628

(22) PCT Filed: Mar. 18, 2009

(86) PCT No.: PCT/EP2009/001987
§ 371 (c)(1),
(2), (4) Date: Dec. 8, 2010

(87) PCT Pub. No.: WO2009/121487
PCT Pub. Date: Oct. 8, 2009

(65) Prior Publication Data
US 2011/0092722 A1 Apr. 21, 2011

(30) Foreign Application Priority Data

Apr. 4, 2008 (DE) .......... 10 2008 017 216

(51) Int. Cl.
*C07C 231/00* (2006.01)
*C07C 231/02* (2006.01)

(52) U.S. Cl.
CPC .................... *C07C 231/02* (2013.01)
USPC ............................... 554/51; 554/35

(58) Field of Classification Search
USPC .................................... 554/35, 51
See application file for complete search history.

(56) References Cited

U.S. PATENT DOCUMENTS

| | | |
|---|---|---|
| 1,972,142 A | 9/1934 | Goldstein |
| 2,601,561 A | 6/1952 | Schertz |
| 3,024,260 A | 3/1962 | Ernst |
| 3,050,418 A | 8/1962 | Mendelsohn et al. |
| 3,113,026 A | 12/1963 | Sprung |
| 3,197,473 A | 7/1965 | Klosa |
| 3,395,162 A | 7/1968 | Lamberti |
| 3,585,224 A | 6/1971 | Friedrich et al. |
| 3,652,434 A | 3/1972 | Bar-Nun et al. |
| 3,652,671 A | 3/1972 | Barron |
| 3,682,946 A | 8/1972 | Liechti |
| 3,836,551 A | 9/1974 | Schroeder et al. |
| 4,133,833 A | 1/1979 | Hull |
| 4,165,311 A | 8/1979 | Isowa et al. |
| 4,221,948 A | 9/1980 | Jean |
| 4,339,648 A | 7/1982 | Jean |
| 4,582,933 A | 4/1986 | Mertens et al. |
| 4,675,319 A | 6/1987 | Nardi et al. |
| 4,859,796 A | 8/1989 | Hurtel et al. |
| 4,994,541 A | 2/1991 | Dell et al. |
| 5,114,684 A | 5/1992 | Walker |
| 5,185,466 A | 2/1993 | Kozulic et al. |
| 5,304,766 A | 4/1994 | Baudet et al. |
| 5,326,538 A | 7/1994 | Walker |
| 5,387,397 A | 2/1995 | Strauss et al. |
| 5,419,815 A | 5/1995 | Doerpinghaus et al. |
| 5,646,318 A | 7/1997 | Dery et al. |
| 5,646,319 A | 7/1997 | Letton et al. |
| 5,710,295 A | 1/1998 | Woodbury et al. |
| 5,830,953 A | 11/1998 | Nishikawa et al. |
| 5,856,538 A | 1/1999 | Strecker et al. |
| 5,866,531 A | 2/1999 | Assmann et al. |
| 5,892,115 A | 4/1999 | Aizawa et al. |
| 5,988,877 A | 11/1999 | Hochrad et al. |
| 6,017,426 A * | 1/2000 | Semeria et al. .......... 204/157.88 |
| 6,107,498 A | 8/2000 | Maisonneuve et al. |
| 6,120,741 A * | 9/2000 | Jacquault et al. ............. 422/199 |
| 6,121,471 A | 9/2000 | Scott |
| 6,127,560 A | 10/2000 | Stidham et al. |
| 6,175,037 B1 | 1/2001 | Tweedy |
| 6,291,712 B1 | 9/2001 | Saihata et al. |
| 6,319,187 B1 | 11/2001 | Scott |
| 6,365,885 B1 | 4/2002 | Roy et al. |
| 6,373,040 B2 | 4/2002 | Thomas |
| 6,614,010 B2 | 9/2003 | Fagrell et al. |

(Continued)

FOREIGN PATENT DOCUMENTS

| | | |
|---|---|---|
| CH | 681586 | 4/1993 |
| CN | 1228910 | 9/1999 |

(Continued)

OTHER PUBLICATIONS

Martinez-Palau et al., Org Thieme Verlag, DE , No. 12, pp. 1847-1849.*

(Continued)

*Primary Examiner* — Deborah D Carr
(74) *Attorney, Agent, or Firm* — Tod A. Waldrop

(57) ABSTRACT

The invention relates to a continuous method for producing fatty acid amides, according to which at least one fatty acid of formula (I),

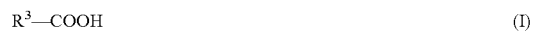

R³—COOH (I)

wherein R³ is an optionally substituted aliphatic hydrocarbon radical, is reacted with at least one amine of formula (II),

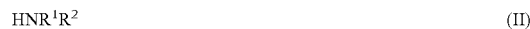

HNR¹R² (II)

wherein R¹ and R² are independently hydrogen or a hydrocarbon radical comprising between 1 and 100 C atoms, to form an ammonium salt, and said ammonium salt is then reacted to form a fatty acid amide, under microwave irradiation in a reaction pipe, the longitudinal axis of the pipe being oriented in the direction of propagation of the microwaves of a monomode microwave applicator.

22 Claims, No Drawings

(56) References Cited

U.S. PATENT DOCUMENTS

| | | |
|---|---|---|
| 6,794,510 B2 | 9/2004 | Le Bourdonnec et al. |
| 6,867,400 B2 | 3/2005 | Collins et al. |
| 6,960,627 B2 | 11/2005 | Huth et al. |
| 6,989,351 B2 | 1/2006 | Collins et al. |
| 7,150,836 B2 | 12/2006 | Meikrantz |
| 7,393,920 B2 | 7/2008 | Collins et al. |
| 7,473,739 B2 | 1/2009 | Dairoku et al. |
| 7,759,454 B2 | 7/2010 | Falk et al. |
| 2003/0021793 A1 | 1/2003 | Hilgers |
| 2005/0027120 A1 | 2/2005 | Gojon-Zorrilla |
| 2005/0272631 A1 | 12/2005 | Miracle et al. |
| 2005/0274065 A1 | 12/2005 | Portnoff et al. |
| 2005/0283011 A1* | 12/2005 | Hoong et al. .................. 554/69 |
| 2006/0057482 A1 | 3/2006 | Yuasa |
| 2006/0228088 A1 | 10/2006 | Charlier de Chily et al. |
| 2006/0252884 A1 | 11/2006 | Falk et al. |
| 2006/0291827 A1 | 12/2006 | Suib et al. |
| 2007/0049721 A1 | 3/2007 | Nefzger et al. |
| 2007/0060762 A1 | 3/2007 | Kawashima et al. |
| 2008/0009541 A1 | 1/2008 | Chambers et al. |
| 2008/0202982 A1 | 8/2008 | Tooley |
| 2008/0264934 A1 | 10/2008 | Moreira et al. |
| 2010/0010244 A1 | 1/2010 | Krull et al. |
| 2010/0032284 A1 | 2/2010 | Krull et al. |
| 2010/0076040 A1 | 3/2010 | Krull et al. |
| 2010/0081843 A1 | 4/2010 | Krull et al. |
| 2010/0116642 A1 | 5/2010 | Krull et al. |
| 2010/0173107 A1 | 7/2010 | Hahn et al. |
| 2011/0083956 A1 | 4/2011 | Krull et al. |
| 2011/0083957 A1 | 4/2011 | Krull et al. |
| 2011/0089019 A1 | 4/2011 | Krull et al. |
| 2011/0089020 A1 | 4/2011 | Krull et al. |
| 2011/0089021 A1 | 4/2011 | Krull et al. |
| 2011/0137081 A1 | 6/2011 | Krull et al. |
| 2012/0088885 A1 | 4/2012 | Krull et al. |
| 2012/0088918 A1 | 4/2012 | Krull et al. |
| 2012/0090983 A1 | 4/2012 | Krull et al. |
| 2012/0095220 A1 | 4/2012 | Krull et al. |
| 2012/0095238 A1 | 4/2012 | Krull et al. |
| 2012/0103790 A1 | 5/2012 | Krull et al. |
| 2012/0178951 A1 | 7/2012 | Krull et al. |
| 2012/0184758 A1 | 7/2012 | Krull et al. |
| 2013/0274368 A1 | 10/2013 | Krull et al. |
| 2013/0289206 A1 | 10/2013 | Krull et al. |
| 2013/0296457 A1 | 11/2013 | Krull et al. |
| 2013/0296458 A1 | 11/2013 | Krull et al. |

FOREIGN PATENT DOCUMENTS

| | | |
|---|---|---|
| CN | 1351954 | 6/2002 |
| CN | 1749279 | 3/2006 |
| CN | 1931980 | 3/2007 |
| DE | 480866 | 8/1929 |
| DE | 1139738 | 11/1962 |
| DE | 2009156 | 7/1970 |
| DE | 2620638 | 11/1977 |
| DE | 3209800 | 9/1983 |
| DE | 224203 | 7/1985 |
| DE | 102005051637 | 5/2007 |
| DE | 102006047619 | 5/2010 |
| DE | 102009001382 | 9/2010 |
| EP | 0134995 | 3/1985 |
| EP | 0207901 | 1/1987 |
| EP | 0226501 | 6/1987 |
| EP | 0383605 | 8/1990 |
| EP | 0437480 | 7/1991 |
| EP | 0722994 | 7/1996 |
| EP | 0377177 | 7/1997 |
| EP | 0884305 | 12/1998 |
| EP | 1256565 | 11/2002 |
| EP | 1291077 | 3/2003 |
| EP | 1435364 | 7/2004 |
| EP | 1491552 | 12/2004 |
| EP | 1712543 | 10/2006 |
| EP | 1775311 | 4/2007 |
| EP | 2079762 | 6/2007 |
| EP | 1849854 | 10/2007 |
| EP | 1884559 | 2/2008 |
| GB | 0385978 | 3/1931 |
| GB | 0414366 | 7/1934 |
| GB | 0719792 | 12/1954 |
| GB | 2094806 | 9/1982 |
| GB | 2095262 | 9/1982 |
| GB | 2361918 | 11/2001 |
| JP | 10330338 | 5/1997 |
| JP | 11508873 | 8/1999 |
| JP | 2003321427 | 11/2003 |
| JP | 2005322582 | 5/2004 |
| JP | 2006181533 | 12/2004 |
| JP | 2005060256 | 3/2005 |
| JP | 2006272055 | 3/2005 |
| JP | 2008031082 | 2/2008 |
| JP | 2009263497 | 11/2009 |
| WO | WO 90/03840 | 4/1990 |
| WO | WO 94/18243 | 8/1994 |
| WO | WO 95/06518 | 3/1995 |
| WO | WO 95/09821 | 4/1995 |
| WO | WO 96/14344 | 5/1996 |
| WO | WO 98/29461 | 7/1998 |
| WO | WO 98/29467 | 7/1998 |
| WO | WO 98/39370 | 9/1998 |
| WO | WO 03/014272 | 2/2003 |
| WO | WO 03/016359 | 2/2003 |
| WO | WO 03/041856 | 5/2003 |
| WO | WO 03/090669 | 11/2003 |
| WO | WO 2004/054707 | 7/2004 |
| WO | WO 2004/072031 | 8/2004 |
| WO | WO 2005/033062 | 4/2005 |
| WO | WO 2005/118526 | 12/2005 |
| WO | WO 2006/024167 | 3/2006 |
| WO | WO 2007/065681 | 6/2007 |
| WO | WO 2007/110384 | 10/2007 |
| WO | WO 2007/126166 | 11/2007 |
| WO | WO 2008/043492 | 4/2008 |
| WO | WO 2008/043493 | 4/2008 |
| WO | WO 2008/043494 | 4/2008 |
| WO | WO 2008/043495 | 4/2008 |
| WO | WO 2009/002880 | 12/2008 |
| WO | WO 2009/064501 | 5/2009 |
| WO | WO 2009/121490 | 10/2009 |

OTHER PUBLICATIONS

Perreux et al.: Tetrahedron, vol. 58, No. 11, 2002, pp. 2155-2162.*
Laurence Perreux, et al., vol. 58, 2155-2162, Dec. 31, 2002).*
International Search Report for PCT/EP2007/008677 Mail dated Mar. 3, 2008.
Translation of International Preliminary Report on Patentability for PCT/EP2007/008677, Mar. 3, 2008.
International Search Report for PCT/EP2007/008678 Mail dated Mar. 10, 2008.
Translation of International Preliminary Report on Patentability for PCT/EP2007/008678, Mar. 10, 2008.
International Search Report for PCT/EP2007/008679 Mail dated Feb. 4, 2008.
International Search Report for PCT/EP2007/008680 Mail dated Feb. 15, 2008.
Translation of International Preliminary Report on Patentability for PCT/EP2007/008680, Feb. 15, 2008.
International Search Report for PCT/EP2007/008681 Mail dated Jan. 29, 2008.
Translation of International Preliminary Report on Patentability for PCT/EP2007/008681, Jan. 29, 2008.
International Search Report for PCT/EP2009/001989 mail dated Jun. 10, 2009.
Translation of International Preliminary Report on Patentability for PCT/EP2009/001989, dated Oct. 14, 2010.
International Search Report for PCT/EP2009/001985 mail dated Jun. 10, 2009.
Translation of International Preliminary Report on Patentability for PCT/EP2009/001985, dated Oct. 14, 2010.

(56) References Cited

OTHER PUBLICATIONS

International Search Report for PCT/EP2009/001986 mail dated Jun. 18, 2009.
Translation of International Preliminary Report on Patentability for PCT/EP2009/001986, dated Oct. 14, 2010.
International Search Report for PCT/EP2009/001987 mail dated Jun. 10, 2009.
Translation of International Preliminary Report on Patentability for PCT/EP2009/001987, dated Oct. 14, 2010.
International Search Report for PCT/EP2009/001984 mail dated Jun. 10, 2009.
Translation of International Preliminary Report on Patentability for PCT/EP2009/001984, dated Oct. 14, 2010.
International Search Report for PCT/EP2009/001990 mail dated Jun. 10, 2009.
Translation of International Preliminary Report on Patentability for PCT/EP2009/001990, dated Dec. 9, 2010.
International Search Report for PCT/EP2009/001988 mail dated Jul. 9, 2009.
Translation of International Preliminary Report on Patentability for PCT/EP2009/001988, dated Jan. 27, 2011.
International Search Report for PCT/EP2010/003443 mail dated Feb. 9, 2011.
Translation of International Preliminary Report on Patentability for PCT/EP2010/003443, dated Feb. 16, 2012.
International Search Report for PCT/EP2010/003442 mail dated Jul. 20, 2010.
Translation of International Preliminary Report on Patentability for PCT/EP2010/003442, dated Feb. 16, 2012.
International Search Report for PCT/EP2010/003445 mail dated Sep. 1, 2010.
Translation of International Preliminary Report on Patentability for PCT/EP2010/003445, dated Jan. 5, 2012.
International Search Report for PCT/EP2010/003444 mail dated Feb. 9, 2011.
Translation of International Preliminary Report on Patentability for PCT/EP2010/003444, dated Jan. 19, 2012.
Response to the Written Opinion in PCT/EP2010/003444, dated Sep. 9, 2011.
International Search Report for PCT/EP2010/003447 mail dated Feb. 9, 2011.
Translation of International Preliminary Report on Patentability for PCT/EP2010/003447, dated Feb. 9, 2012.
Written Opinion of the IPEA for PCT/EP2010/003447, dated Sep. 9, 2011.
International Search Report for PCT/EP2010/003446 mail dated Feb. 9, 2011.
Translation of International Preliminary Report on Patentability for PCT/EP2010/003446, dated Jan. 19, 2012.
T. Cablewski, et al: "Development and Application of a Continuous Microwave Reactor for Organic Synthesis" Journal of Organic Chemistry, American Chemical Society, Easton.; US, vol. 59, Jan. 1, 1994, pp. 3408-3412, XP000198783.
Glasnov, et al: "Microwave-assisted synthesis under continuous-flow conditions", Macromolecular Rapid Communications, 28(4), 395-410 CODEN: MRCOE3; Jan. 1, 2007, XP002529633.
L. Perreux, et al: "Solvent-free preparation of amides from acids and primary amines under microwave irradiation", Tetrahedron, Elsevier Science Publishers, Amsterdam, NL, vol. 58, No. 11, Mar. 11, 2002, pp. 2155-2162, XP004343866.
C. Ferroud, et al: "Microwaves-assisted solvent-free synthesis of N-acetamides by amidation or aminolysis", Tetrahedron Letters., vol. 49, Mar. 6, 2008, pp. 3004-3008, XP022602751 NL Elsevier, Amsterdam.
B. Toukoniitty, et al: "Esterification of propionic acid under microwave irradiation over an ion-exchange resin", Catalysis Today, Elsevier, NL, vol. 100, No. 3-4, Feb. 28, 2005, pp. 431-435, XP004850051.
Chemat, et al: "The role of selective heating in the microwave activation of heterogeneous catalysis reactions using a continuous microwave reactor", Journal of Microwave Power and Electromagnetic Energy, The Institute, Vienna, VA, US, vol. 33, No. 2, Jan. 1, 1998, pp. 88-94, XP009143773.
Konrad G, Kabza, et al: "Microwave-Induced Esterification Using Heterogeneous Acid Catalyst in a Low Dielectric Constant Medium", Journal of Organic Chemistry, American Chemical Society, Easton.; US, vol. 65, Jan. 1, 2000, pp. 1210-1214, XP007916930.
Erik Esveld, et al: "Pilot Scale Continuous Microwave Dry-Media Reactor. Part 1: Design and Modeling", Chemical Engineering and Technology, Weinheim, DE, vol. 23, No. 3, Jan. 1, 2000, pp. 279-283, XP007916923.
Erik Esveld, et al: "Pilot Scale Continuous Microwave Dry-Media Reactor Part II: Application to Waxy Esters Production", Chemical Engineering and Technology, Weinheim, DE, vol. 23, No. 5, Jan. 1, 2000, pp. 429-435, XP007916803.
Noel S. Wilson, et al: "Development and Applications of a Practical Continuous Flow Microwave Cell", Organic Process Research and Development, American Chemical Society, US, vol. 8, No. 3, Jan. 1, 2004, pp. 535-538, XP007916928.
G. Pipus, et al: "Esterification of benzoic acid in microwave tubular flow reactor", Chemical Engineering Journal, Elsevier Sequoia, Lausanne, CH, vol. 76, Jan. 1, 2000, pp. 239-245, XP007916929.
L. Perreux, et al: "Microwave effects in solvent-free esters aminolysis" Tetrahedron, Elsevier Science Publishers, Amsterdam, NL, vol. 59, No. 12, Mar. 17, 2003, pp. 2185-2189, XP004414169.
R. S. Varma, et al: "Solvent-free synthesis of amides from non-enolizable esters and amines using microwave irradiation" Tetrahedron Letters, Elsevier, Amsterdam, NL, vol. 40, No. 34, Aug. 20, 1999, pp. 6177-6180, XP004174006.
R. Jachuck, et al: "Process intensification: oxidation of benzyl alcohol using a continuous isothermal reactor under microwave irradiation", Green Chemistry, Royal Society of Chemistry, Cambridge, GB, vol. 8, Jan. 1, 2006, pp. 29-33, XP007916789.
J. Ruhoff, et al., J. Am. Chem. Soc., 59 (1937), 401-402.
C. Chen et al., J. Chem. Soc., Chem. Commun., 1990, 807-809.
Katritzky et al. (Energy & Fuels 4 (1990), 555-561).
An et al. (J. Org. Chem. (1997), 62, 2505-2511).
Pipus et al. (First European Congress on Chemical Engineering, Firenze, Italy, May 4-7, 1997; AIDIC: Milan, Italy, 1997; pp. 45-48).
Amore et al. (Macromolecular Rapid Communications, vol. 28 (2007), Issue 4, pp. 473-477).
Q. Yang et al. (Synth. Commun. 2008, 38, 4107-4115).
Zradni et al. (Synth. Commun. 2002, 32, 3525-3531).
J. Kremsner, et al, Top Curr Chem, (2006) 266: pp. 233-278.
Energieeintrag im Discover, "Flexibilitaet ist Trumpf", http://www.cem.de/documents/produlde/mikro_synthese/allgemeines/flexibel.htm, Jun. 2009.
D. Bogdal, Microwave-assisted Organic Synthesis, Elsevier 2005.
K. Lange, K.H. Löcherer, Taschenbuch der Hochfrequenztechnik [Pocket book of high-frequency technology], vol. 2, p. K21 ff.
"Microwave vs. Conventional Heating", webpage, www.biotage.com, Jan. 2009.
Kumar, et al., "Microwave Assisted Direct Synthesis of 2-Substituted Benzoxazoles From Carboxylic Acids Under Catalyst and Solvent-Free Conditions", SYNLETT, No. 9, 2005, pp. 1401-1404.
"Microwave Synthesis" by B. L. Hayes, CEM Publishing 2002.
Goretzki et al., Macromol. Rapid Commun. 2004, 25, 513-516.
Gelens et al., Tetrahedron Letters 2005, 46(21), 3751-3754.
M. S. Nery, et al., "Niobium pentachloride promoted conversion of carboxylic acids to carboxamides: Synthesis of the 4-aryl-1,2,3,4-tetrahydrolsoquinollne alkaloid structures" Synthesis, (2),272-276, 2003.
Vazquez-Tato, M.P., "Microwave-Mediated Synthesis of Amides", SYNLETT, No. 7, 1993, p. 506.
X. Wu, et al., "Microwave Enhanced Aminocarbonylations in Water", Organic Letters, 7(15), pp. 3327-3329, 2005.
Massicot et al., Synthesis 2001 (16), 2441-2444.
Iannelli et al., Tetrahedron 2005, 61, 1509-1515.
R. Martinez-Palou, et al., "Synthesis of Long Chain 2-Alkyl-1-(2-hydroxyethyl)-2-imidazolines Under Microwave in Solvent-Free Conditions", SYNLETT 2003, No. 12, pp. 1847-1849.

(56) References Cited

OTHER PUBLICATIONS

R. Plantier-Royon, et al., "Synthesis of Functionalized Bis-Amides of L-(+)-Tartaric Acid and Application as Copper(II) Ligands", C.R. Chimie, 2004, pp. 119-123.
R.S. Hunter, "Conversion of Visual to Instrumental Measurements of Yellowness", 1981, JAOCS, May, pp. 606-612.
Synthewave 402 Manual, 2000, Prolabo, Support pp. 2 and Manual pp. 1-13 (total 15 pages).
Beilstein Substance Identification, BRN No. 6190607, 1981.
S. Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.
H.J. Bauer, et al., Makromol. Chem., 183, 1982, pp. 2971-2976.
English Abstract of JP52125142, Oct. 20, 1977.
English Abstract of JP54005931, Jan. 17, 1979.
English Abstract of DD224203, Jul. 3, 1985.
English Abstract of EP1291077, Mar. 12, 2003.
International Search Report for PCT/EP201/005427 mail dated Mar. 21, 2011.
Translation of International Preliminary Report on Patentability for PCT/EP2010/005427 mail dated Mar. 21, 2011.
International Search Report for PCT/EP201/005428 mail dated Jan. 27, 2011.
Translation of International Preliminary Report on Patentability for PCT/EP2010/005428 mail dated Dec. 21, 2001.
Translation of SIPO Office Action for Application 200980101830.0, May 12, 2012.
Translation of SIPO Search Report for Application 200980101830.0, May 12, 2012.
"Fatty Acids and Chemical Specialties", pp. 131-147, 1955.
English Translation of CN 1351954.
M. Hajek in A. Loupe "Microwaves In Organic Synthesis", Wiley, 2006, Chapter 13, pp. 615-652.
Shore, et al, "Catalysis in Capillaries by Pd Thin Films Using Microwave-Assisted Continuous-Flow Organic Synthesis (MACOS)" Angewandte Chemie 2006, 118, pp. 2827-2832.
AOSTRA Journal of Research 3 (1986) "Microwave Assisted Catalytic Conversion of Cyclohesxene" pp. 53-59.
C. Mazzocchia et al., "Fatty acid methyl esters synthesis from triglycerides over heterogeneous catalysts in the presence of microwaves" C.R. Chimie 7 (2004) pp. 601-605.
V. Lertsathapornsuk et al, "Microwave assisted in continous biodiesel production from waste frying palm oil and its performance in a 100 kW diesel generator" Fuel Processing Technology 89 (2008) pp. 1330-1336, XP025681095.
N. Azcan et al, "Microwave assisted transesterification of rapeseed oil" Fuel 87 (2008) pp. 1781-1788, XP022611169.
N. Azcan et al, "Alkali catalyzed transesterification of cottonseed oil by microwave irradiation" Fuel 86 (2007) pp. 2639-2644, XP022322088.
N. Leadbeater et al, "Fast, Easy Preparation of Biodiesel Using Microwave Heating" Energy & Fuels 2006, 20, pp. 2281-2283.
Leadbeater, et al, "Continuous-Flow Preparation of Biodiesel Using Microwave Heating:, Energy & Fuels 2007, 21, pp. 1777-1781.
A. Breccia et al, "Reaction Between Methanol And Commercial Seed Oils Under Microwave Irradiation" Internation Microwave Power Institute 1999, 34, pp. 3-8.
N. Saifuddin et al, "Production Of Ethyl Ester (Biodiesel) from used Frying Oil: Optimization of Transesterification Process using Microwave Irradiation" Malaysian Journal of Chemistry, 2004, vol. 6, pp. 77-82.
Arora et al, "A mild and efficient procedure for the conversion of aromatic carboxylic acid esters to secondary amides" Can. J. Chem, vol. 83 (2005), pp. 1137-1140.
English Abstract for CH 681586, Apr. 15, 1993.
English Abstract for DE 2620638, Nov. 24, 1977.
English Abstract for DE 102005051637, May 3, 2007.
English Abstract for EP 1256565, Nov. 13, 2002.
English Abstract for JP 2005060256, Mar. 10, 2005.
English Abstract for JP 2003321427, Nov. 11, 2003.
English Abstract for JP 2008031082, Feb. 14, 2008.
International Search Report for PCT/EP2010/005427 dated Mar. 21, 2011.
Translation of International Preliminary Report on Patentability for PCT/EP2010/005427, dated Mar. 21, 2011.
International Search Report for PCT/2010/005428 dated Jan. 27, 2011.
Translation of International Preliminary Report on Patentability for PCT/EP2010/005428, dated Jan. 27, 2011.
International Search Report for PCT/EP2011/006173 mail dated May 8, 2012.
Translation of International Preliminary Report on Patentability for PCT/EP2011/006173, dated Jul. 4, 2013.
International Search Report for PCT/EP2011/006172 mail dated Jul. 10, 2012.
Translation of International Preliminary Report on Patentability for PCT/EP2011/006172, dated Jul. 4, 2013.
International Search Report for PCT/EP2011/006175 mail dated May 9, 2012.
Translation of International Preliminary Report on Patentability for PCT/EP2011/006175, dated Jul. 4, 2013.
International Search Report for PCT/EP2011/006174 mail dated Jul. 10, 2012.
Translation of International Preliminary Report of Patentability for PCT/EP2011/006174, dated Jul. 4, 2013.
International Search Report for PCT/EP2011/006176 mail dated Aug. 1, 2012.
Translation of International Preliminary Report on Patentability for PCT/EP2011/006176, dated Jul. 4, 2013.
"Objective Colour Assessment and Quality Control in the Chemical, Pharmaceutical and Cosmetic Industries", Application Report No. 3.9 e from Hach Lange, pp. 1-28, Feb. 2013.
Advanced Organic Chemistry: Reactions, Mechanisms, and Structure: Second Edition, Jerry March, Wiley-Interscience Publication, pp. 321-331 and 382-389, 1977.
Zhaoju Yu et al: "Biodegradable polyvinyl alcohol)-graftpoly(epsilon-caprolactone) comb-like polyester: Microwave synthesis and its characterization", Journal of Applied Polymer Science, vol. 104, No. 6, Jun. 15, 2007, pp. 3973-3979, XP55023817.
English translation of DIN Standard 6162, Mar. 2013.
Englsh Abstract for WO 03/090669, Nov. 6, 2003.
English translation of JP 2009 263 497, 2009.
Ella Bezdushna et al: "Microwave-Assisted Esterification of Methacrylic Acid and Polymer-Analogous Esterification of Poly[ethylene-co-(acrylic acid)] with Dissimilar Phenols", Macromolecular Rapid Communications, vol. 208, No. 4, Feb. 19, 2007, pp. 443-448, XP55023715.
Karl G. Kempf et al: "A Procedure for Preparing Aryl Esters of Polyacids. The Conversion of Poly(methacrylic acid) to Poly(phenyl methacrylate)", Macromolecules, vol. 11, No. 5, Sep. 1, 1978, pp. 1038-1041, XP55024162.
English Abstract for EP 0134995, Mar. 27, 1985.
Pollington, Journal of Organic Chemistry, vol. 56, pp. 1313-1314, 1991.
Ella Bezdushna et al, Macromolecular Chemistry & Physics, vol. 209, pp. 1942-1947, XP55023715, 2008.
English Abstract for DE 10 2009 001 382, Sep. 9, 2010.
Oliver Kretschmann et al: Microwave-Assisted Synthesis of Associative Hydrogels., Macromolecular Rapid Communications, vol. 28, No. 11, Jun. 1, 2007, pp. 1265-1269, XP55023774.
Sebastian Sinnwell et al: "Microwave assisted hydroxyalkylamidation of poly(ethylene-co-acrylic acid) and formation of grafted poly([epsilon]-caprolactone) side chains", Journal of Polymer Science Part A: Polymer Chemistry, vol. 45, No. 16, Aug. 15, 2007, pp. 3659-3667, XP55024233.
Barbosa et al, "Niobium to alcohol mol ratio control of the concurring esterification and etherification reactions promoted by NbCl5 and Al2O3 catalysts under microwave irradiation," App. Catalysis A: General vol. 338, pp. 9-13 (2008).

(56) References Cited

OTHER PUBLICATIONS

Arfan et al, "Efficient Combination of Recyclable Task Specific Ionic Liquid and Microwave Dielectric Heating for the Synthesis of Lipophilic Esters," Organic Process Research & Development vol. 9, pp. 743-748 (2005).

Essen et al, "The Velocity of Propagation of Electromagnetic Waves Derived from the Resonant Frequencies of a Cylindrical Cavity Resonator," Proc. R. Soc. Lond. A (1948), vol. 194, pp. 348-361.

Vacek et al, "Selective enzymic esterification of free fatty acids with n-butanol under microwave irradiation and under classical heating," Biotechnology Letters, vol. 22, pp. 1565-1570 (2000).

Mohan et al, "Zeolite catalyzed acylation irradiation and amines with acetic acid under microwave irradiation," Green Chem. 2006, vol. 8, pp. 368-372.

Machetti et al., "Parallel Synthesis of an Amide Library Based on the 6,8-Dioxa-3-azabicyclo[3.2.1.]octane Scaffold by Direct Aminolysis of Methyl Esters," J. Comb. Chem., 2007, vol. 9, pp. 454-461.

Petricci et al, "Microwave-assisted acylation of amines, alcohols, and phenols by the use of solid-supported reagents (SSRs)," J. Org. Chem. vol. 69, pp. 7880-7887, (2004).

Katritzky et al, "Efficient microwave access to polysubstituted amidines from imidoylbenzotriazoles," J. Org. Chem. vol. 71, pp. 3375-3380 (2006).

Werner et al, "Design and synthesis of a 3,4-dehydroproline amide discovery library," J. Comb. Chem. (2007), 9(4), pp. 677-683.

Fats and Oils: Formulating and Processing for Applications, Second Ed., O'Brien, CRC Press 2003, Ch. 3, sec. 3.4.2., lines 12-13.

KIC Chemicals Inc., Capric Acid, available online at http://www.kicgroup.com/capric.htm, 2013.

Fatty Acids Division, Soap Association, "Fatty Acids for Chemical Specialties: A symposium of the Soap, Detergents, and Sanitary Chemical Products Division of the Chemical Specialties Manufacturers Association," 1955, pp. 131-147, available online at http://www.aciscience.org/Oleochemical/FattyAcid.aspx.

Zradini, et al, "Minutes Synthesis of Amides from Esters and Amines Under Microwave Irradiation," Fifth International Electronic Conference on Synthetic Organic Chemistry (ECSOC-5), avaiable at http://www.mdpi.org/ecsoc/ecsoc-5/Papers/e0013/e0013.html, 2001.

Mazzocchia, C., et al., Fast synthesis of biodiesel from trygycerides in presence of microwave, 2006, Advances in Microwave and Radio Frequency Processing, Report of the 8th international conference on microwave and high frequency heatting held in Bayrueth, Germany, Sep. 2001, Springer Berlin Heidelberg, Part V, pp. 370-376 (18 pages).

Ishihara et al, "3,4,5-Trifluorobenzeneboronic Acid as an Extremely Active Amidation Catalyst," J. Org. Chem. vol. 1, (1996), pp. 4196-4197.

Gonzalez et al, "Tartradiamide formation by thermolysis of tartaric acid with alkylamines," Tetrahedron Letters vol. 49 (2008 3925-3926.

(Hawley's Condensed Chemical Dictionary, 14th ed., Lewis, Richard J. Sr. ed., copyright 2002 John Wiley & Sons, Inc., available online at http://www.knovel.comiwebiportalibrowseidisplay? EXT KNOVEL DISPLAY bookid=704&VerticalID=0.

Reddy et al, "Zirconyl chloride promoted highly efficient solid phase synthesis of amide derivatives," Chinese Chemical Letters, vol. 18 (2007), pp. 1213-1217.

Bose et al, "Microwave promoted energy-efficient N-formylation with aqueous formic acid," Tetrahedron Let. vol. 47 (2006), pp. 4605-4607.

Jain et al, "Acetylation of some organic compounds under microwave irradiation," J. Indian Chem. Soc., vol. 84, Feb. 2007, p. 188.

DiLuca et al, "A new, simple procedure for the synthesis of formyl amides," Synlett No. 14 (2004), pp. 2570-257.

Desai et al, "Thermal and microwave-assisted N-formylation using solid-supported reagents," Tetrahedron Let. vol. 46 (2005), pp. 955-957.

English Abstract for CN 1931980, Mar. 2007.

Kangani, et al., "One Pot direct synthesis of amides or oxazolines from carboxylic acids uding Deoxo-Fluor reagent," Tetrahedron Letters, vol. 46, (2005), pp. 8917-8920.

English Abstract for JP 2005322582, May 2005.

English Abstract for JP 2006272055, Mar. 2005.

English Abstract for JP 2006181533, Dec. 2004.

English Abstract for JP 10330338, May 1997.

English Abstract for DE480866, Aug. 1929.

* cited by examiner

CONTINUOUS METHOD FOR PRODUCING FATTY ACID AMIDES

Fatty acid amides find various uses as chemical raw materials, for example in the production of pharmaceuticals and agrochemicals. Carboxamides bearing at least one relatively long alkyl radical are of very great industrial interest owing to their surface-active properties and are used, inter alia, as a constituent of washing and cleaning compositions and in cosmetics. They are also used successfully as assistants in metalworking, in the formulation of crop protection compositions and in the delivery and processing of mineral oil.

More particularly, fatty acid amides which bear additional functional groups with basic character are very sought-after as precursors for preparation of surface-active substances. These are, for example, fatty acid derivatives which bear an alkyl radical which is bonded via an amide group and which is itself substituted by at least one tertiary amino group which imparts basic character. Such amides have a greatly increased hydrolysis stability compared to corresponding esters. By alkylation with alkylating agents, they can be converted to cationic surfactants. By reaction with alkylating agents bearing acid groups, what are known as betaines are obtainable therefrom; oxidation reactions with peroxides lead to the group of the amine oxides, a product group which can likewise be considered to be amphoteric. Amine oxides and betaines find a high degree of use as raw materials for the production of washing compositions, cleaning concentrates, detergents, cosmetics and pharmaceuticals, as emulsifiers and in the mineral oil industry as corrosion or gas hydrate inhibitors.

The industrial preparation of fatty acid amides typically involves reacting a reactive derivative of a fatty acid, such as acid anhydride, acid chloride or ester, with an amine, or in situ activation of the carboxylic acid by the use of coupling reagents, for example N,N'-dicyclohexylcarbodiimide, or working with very specific and hence expensive catalysts. This leads firstly to high production costs and secondly to undesired accompanying products, for example salts or acids which have to be removed and disposed of or worked up. For example, the Schotten-Baumann synthesis, by which numerous carboximides are prepared on the industrial scale, forms equimolar amounts of sodium chloride. However, the residues of the auxiliary products and by-products which remain in the products can cause very undesired effects in some cases. For example, halide ions and also acids lead to corrosion; some of the coupling reagents and the by-products formed thereby are toxic, sensitizing or carcinogenic.

The desirable direct thermal condensation of fatty acid and amine requires very high temperatures and long reaction times, and does not lead to satisfactory results since different side reactions reduce the yield. These include, for example, decarboxylation of the carboxylic acid, oxidation of the amino group during long heating, thermal disproportionation of secondary amines to primary and tertiary amine, and especially the thermally induced degradation of the amino group. An additional problem is the corrosiveness of the reaction mixtures composed of acid, amine, amide and water of reaction, which often severely attack or dissolve metallic reaction vessels at the high reaction temperatures required. The metal contents introduced into the products as a result are very undesired since they impair the product properties not only with regard to the color thereof, but also catalyze decomposition reactions and hence reduce the yield. The latter problem can be partly avoided by means of specific reaction vessels made of highly corrosion-resistant materials, or with appropriate coatings, which, however, requires long reaction times and hence leads to products of impaired color. As a result, it is impossible to prepare colorless products which are desired especially for cosmetic applications, with iodine color numbers of, for example, less than 6. The latter requires either the use of color-improving additives during the thermal amidation reaction and/or additional process steps, for example bleaching, which, however, itself requires the addition of further assistants and often leads to an equally undesired impairment of the odor of the amides.

A more recent approach to the synthesis of amides is the microwave-supported conversion of carboxylic acids and amines to amides Vázquez-Tato, Synlett 1993, 506, discloses the use of microwaves as a heat source for the preparation of amides from carboxylic acids and arylaliphatic amines via the ammonium salts. The syntheses were effected there on the mmol scale.

Perreux et al., Tetrahedron 58 (2002), 2155-2162, discloses the solvent-free synthesis of different amides from carboxylic acids and amines under microwave irradiation. There too, the mmol scale was employed.

Gelens et al., Tetrahedron Letters 2005, 46(21), 3751-3754, discloses a multitude of amides which have been synthesized with the aid of microwave radiation. The syntheses were effected in 10 ml vessels.

The scaleup of such microwave-supported reactions from the laboratory to an industrial scale and hence the development of plants suitable for production of several tonnes, for example several tens, several hundreds or several thousands of tonnes, per year with space-time yields of interest for industrial scale applications has, however, not been achieved to date. One reason for this is the penetration depth of microwaves into the reaction mixture, which is typically limited to several millimeters to a few centimeters, and causes restriction to small vessels especially in reactions performed in batchwise processes, or leads to very long reaction times in stirred reactors. The occurrence of discharge processes and plasma formation places tight limits on an increase in the field strength, which is desirable for the irradiation of large amounts of substance with microwaves, especially in the multimode units used with preference to date for scaleup of chemical reactions. Moreover, the inhomogeneity of the microwave field, which leads to local overheating of the reaction mixture and is caused by more or less uncontrolled reflections of the microwaves injected into the microwave oven at the walls thereof and the reaction mixture, presents problems in the scaleup in the multimode microwave units typically used. In addition, the microwave absorption coefficient of the reaction mixture, which often changes during the reaction, presents difficulties with regard to a safe and reproducible reaction regime. Chen et al., J. Chem. Soc., Chem. Commun., 1990, 807-809, describe a continuous laboratory microwave reactor, in which the reaction mixture is conducted through a Teflon pipe coil mounted in a microwave oven. A similar continuous laboratory microwave reactor is described by Cablewski et al., J. Org. Chem. 1994, 59, 3408-3412 for performance of a wide variety of different chemical reactions. In neither case, however, does the multimode microwave allow upscaling to the industrial scale range. The efficacy thereof with regard to the microwave absorption of the reaction mixture is low owing to the microwave energy being more or less homogeneously distributed over the applicator space in multimode microwave applicators and not focused on the pipe coil. A significant increase in the microwave power injected leads to undesired plasma discharges. In addition, the spatial inhomogeneities in the microwave field which change with time and are referred to as hotspots make a safe and reproducible reaction regime on a large scale impossible.

Additionally known are monomode or single-mode microwave applicators, in which a single wave mode is employed, which propagates in only one three-dimensional direction and is focused onto the reaction vessel by waveguides of exact dimensions. These instruments do allow high local field strengths, but, owing to the geometric requirements (for example, the intensity of the electrical field is at its greatest at the wave crests thereof and approaches zero at the nodes), have to date been restricted to small reaction volumes (≤50 ml) on the laboratory scale.

A process was therefore sought for preparing fatty acid amides, in which fatty acid and amine can also be converted on the industrial scale under microwave irradiation to the amide. There was a particular interest in preparation processes for tertiary amides, and for amides which bear tertiary amino groups. At the same time, maximum, i.e. up to quantitative, conversion rates and yields shall be achieved. The process shall additionally enable a very energy-saving preparation of the fatty acid amides, which means that the microwave power used shall be absorbed substantially quantitatively by the reaction mixture and the process shall thus give a high energetic efficiency. At the same time, only minor amounts of by-products, if any, shall be obtained. The amides shall also have a minimum metal content and a low intrinsic color. In addition, the process shall ensure a safe and reproducible reaction regime.

It has been found that, surprisingly, fatty acid amides can be prepared in industrially relevant amounts by direct reaction of fatty acids with amines in a continuous process by only briefly heating by means of irradiation with microwaves in a reaction tube whose longitudinal axis is in the direction of propagation of the microwaves of a monomode microwave applicator. At the same time, the microwave energy injected into the microwave applicator is virtually quantitatively absorbed by the reaction mixture. The process according to the invention additionally has a high level of safety in the performance and offers high reproducibility of the reaction conditions established. The amides prepared by the process according to the invention exhibit a high purity and low intrinsic color not obtainable in comparison to by conventional preparation processes without additional process steps.

The invention provides a continuous process for preparing fatty acid amides by reacting at least one fatty acid of the formula I $$R^3\text{—COOH} \tag{I}$$

in which $R^3$ is an optionally substituted aliphatic hydrocarbon radical having 5 to 50 carbon atoms
with at least one amine of the formula II $$HNR^1R^2 \tag{II}$$

in which $R^1$ and $R^2$ are each independently hydrogen or a hydrocarbon radical having 1 to 100 carbon atoms
to give an ammonium salt and then converting this ammonium salt to the fatty acid amide under microwave irradiation in a reaction tube whose longitudinal axis is in the direction of propagation of the microwaves from a monomode microwave applicator.

The invention further provides fatty acid amides with low metal content, prepared by reaction of at least one fatty acid of the formula I $$R^3\text{—COOH} \tag{I}$$

in which $R^3$ is hydrogen or an optionally substituted aliphatic hydrocarbon radical having 5 to 50 carbon atoms,
with at least one amine of the formula $$HNR^1R^2 \tag{II}$$

in which $R^1$ and $R^2$ are each independently hydrogen or a hydrocarbon radical having 1 to 100 carbon atoms,
to give an ammonium salt and then converting this ammonium salt to the fatty acid amide under microwave irradiation in a reaction tube longitudinal axis whose is in the direction of propagation of the microwaves from a monomode microwave applicator.

Suitable fatty acids of the formula I are generally compounds which have at least one carboxyl group on an optionally substituted aliphatic hydrocarbon radical having 5 to 50 carbon atoms. In a preferred embodiment, the aliphatic hydrocarbon radical is an unsubstituted alkyl or alkenyl radical. In a further preferred embodiment, the aliphatic hydrocarbon radical bears one or more, for example two, three, four or more, further substituents. Suitable substituents are, for example, halogen atoms, $C_1$-$C_5$-alkoxy, for example methoxy, poly($C_1$-$C_5$-alkoxy), poly($C_1$-$C_5$-alkoxy)alkyl, carboxyl, ester, amide, cyano, nitrile, nitro, sulfo and/or aryl groups having 5 to 20 carbon atoms, for example phenyl groups, with the proviso that they are stable under the reaction conditions and do not enter into any side reactions, for example elimination reactions. The $C_5$-$C_{20}$ aryl groups may themselves in turn bear substituents, for example halogen atoms, halogenated alkyl radicals, $C_1$-$C_{20}$-alkyl, $C_2$-$C_{20}$-alkenyl, $C_1$-$C_5$-alkoxy, for example methoxy, ester, amide, cyano, nitrile and/or nitro groups. However, the aliphatic hydrocarbon radical bears at most as many substituents as it has valences. In a specific embodiment, the aliphatic hydrocarbon radical $R^3$ bears further carboxyl groups. Thus, the process according to the invention is equally suitable for amidating polycarboxylic acids having, for example, two, three, four or more carboxyl groups. The reaction of polycarboxylic acids with primary amines by the process according to the invention can also form imides.

Particular preference is given to fatty acids (I) which bear an aliphatic hydrocarbon radical having 6 to 30 carbon atoms and especially having 7 to 24 carbon atoms, for example having 8 to 20 carbon atoms. They may be of natural or synthetic origin. The aliphatic hydrocarbon radical may also contain heteroatoms, for example oxygen, nitrogen, phosphorus and/or sulfur, but preferably not more than one heteroatom per three carbon atoms.

The aliphatic hydrocarbon radicals may be linear, branched or cyclic. The carboxyl group may be bonded to a primary, secondary or tertiary carbon atom. It is preferably bonded to a primary carbon atom. The hydrocarbon radicals may be saturated or unsaturated. Unsaturated hydrocarbon radicals contain one or more C=C double bonds and preferably one, two or three C=C double bonds. There is preferably no double bond in the α,β position to the carboxyl group. For instance, the process according to the invention has been found to be particularly useful for preparation of amides of polyunsaturated fatty acids, since the double bonds of the unsaturated fatty acids are not attacked under the reaction conditions of the process according to the invention. Preferred cyclic aliphatic hydrocarbon radicals possess at least one ring with four, five, six, seven, eight or more ring atoms.

Suitable fatty acids are, for example, pentanoic acid, pivalic acid, hexanoic acid, cyclohexanoic acid, heptanoic acid, octanoic acid, nonanoic acid, neononanoic acid, decanoic acid, neodecanoic acid, undecanoic acid, neoundecanoic acid, dodecanoic acid, tridecanoic acid, tetradecanoic acid, 12-methyltridecanoic acid, pentadecanoic acid, 13-methyltetradecanoic acid, 12-methyltetradecanoic acid, hexadecanoic acid, 14-methylpentadecanoic acid, heptadecanoic acid, 15-methylhexadecanoic acid, 14-methylhexadecanoic acid, octadecanoic acid, isooctadecanoic acid, eicosanoic acid, docosanoic acid and tetracosanoic acid, and also myristoleic acid, palmitoleic acid, hexadecadienoic acid, delta-9-cis-heptadecenoic acid, oleic acid, petroselic acid, vaccenic acid, linoleic acid, linolenic acid, gadoleic acid, gondoic acid, eicosadienoic acid, arachidonic acid, cetoleic acid, erucic acid, docosadienoic acid and tetracosenoic acid, and also dodecenylsuccinic acid, octadecenylsuccinic acid and mixtures thereof. Additionally suitable are fatty acid mixtures obtained from natural fats and oils, for example cottonseed oil, coconut oil, groundnut oil, safflower oil, corn oil, palm kernel oil, rapeseed oil, olive oil, mustardseed oil, soya oil, sunflower oil, and also tallow oil, bone oil and fish oil. Fatty acids or fatty acid mixtures likewise suitable for the process according to the invention are tall oil fatty acids, and also resin acids and naphthenic acids.

The process according to the invention is preferentially suitable for preparation of secondary amides, i.e. for reaction of fatty acids with amines in which $R^1$ is a hydrocarbon radical having 1 to 100 carbon atoms and $R^2$ is hydrogen.

The process according to the invention is more preferentially suitable for preparation of tertiary amides, i.e. for reaction of fatty acids with amines in which both $R^1$ and $R^2$ radicals are independently a hydrocarbon radical having 1 to 100 carbon atoms. The $R^1$ and $R^2$ radicals may be the same or different. In a particularly preferred embodiment, $R^1$ and $R^2$ are the same.

In a first preferred embodiment, $R^1$ and/or $R^2$ are each independently an aliphatic radical. It has preferably 1 to 24, more preferably 2 to 18 and especially 3 to 6 carbon atoms. The aliphatic radical may be linear, branched or cyclic. It may additionally be saturated or unsaturated, preferably saturated. The hydrocarbon radical may bear substituents, for example $C_1$-$C_5$-alkoxyalkyl, cyano, nitrile, nitro and/or $C_5$-$C_{20}$-aryl groups, for example phenyl radicals. The $C_5$-$C_{20}$-aryl radicals may in turn optionally be substituted by halogen atoms, halogenated alkyl radicals, $C_1$-$C_{20}$-alkyl, $C_2$-$C_{20}$-alkenyl, $C_1$-$C_5$-alkoxy, for example methoxy, ester, amide, cyano, nitrile and/or nitro groups. Particularly preferred aliphatic radicals are methyl, ethyl, n-propyl, isopropyl, n-butyl, isobutyl and tert-butyl, n-hexyl, cyclohexyl, n-octyl, n-decyl, n-dodecyl, tridecyl, isotridecyl, tetradecyl, hexadecyl, octadecyl and methylphenyl. In a particularly preferred embodiment, $R^1$ and/or $R^2$ are each independently hydrogen, a $C_1$-$C_6$-alkyl, $C_2$-$C_6$-alkenyl or $C_3$-$C_6$-cycloalkyl radical, and especially an alkyl radical having 1, 2 or 3 carbon atoms. These radicals may bear up to three substituents.

In a further preferred embodiment, $R^1$ and $R^2$ together with the nitrogen atom to which they are bonded form a ring. This ring has preferably 4 or more, for example 4, 5, 6 or more, ring members. Preferred further ring members are carbon, nitrogen, oxygen and sulfur atoms. The rings may themselves in turn bear substituents, for example alkyl radicals. Suitable ring structures are, for example, morpholinyl, pyrrolidinyl, piperidinyl, imidazolyl and azepanyl radicals.

In a further preferred embodiment, $R^1$ and/or $R^2$ are each independently an optionally substituted $C_6$-$C_{12}$ aryl group or an optionally substituted heteroaromatic group having 5 to 12 ring members.

In a further preferred embodiment, $R^1$ and/or $R^2$ are each independently an alkyl radical interrupted by a heteroatom. Particularly preferred heteroatoms are oxygen and nitrogen.

For instance, $R^1$ and $R^2$ are preferably each independently radicals of the formula III $$-(R^4-O)_n-R^5 \qquad (III)$$

in which $R^4$ is an alkylene group having 2 to 6 carbon atoms, and preferably having 2 to 4 carbon atoms, for example ethylene, propylene, butylene or mixtures thereof, $R^5$ is a hydrocarbon radical having 1 to 24 carbon atoms or a group of the formula $-NR^{10}R^{11}$, n is an integer from 2 to 500 and, preferably from 3 to 200 and especially from 4 to 50, for example from 5 to 20, and $R^{10}$, $R^{11}$ are each independently an aliphatic radical having 1 to 24 carbon atoms and preferably 2 to 18 carbon atoms, an aryl group or heteroaryl group having 5 to 12 ring members, a poly(oxyalkylene) group having 1 to 50 poly(oxyalkylene) units, where the poly(oxyalkylene) units derive from alkylene oxide units having 2 to 6 carbon atoms or $R^{10}$ and $R^{11}$ together with the nitrogen atom to which they are bonded form a ring having 4, 5, 6 or more ring members.

Additionally preferably, $R^1$ and/or $R^2$ are each independently radicals of the formula IV $$-[R^6-N(R^7)]_m-(R^7) \qquad (IV)$$

in which $R^6$ is an alkylene group having 2 to 6 carbon atoms and preferably having 2 to 4 carbon atoms, for example ethylene, propylene or mixtures thereof, each $R^7$ is independently hydrogen, an alkyl radical having up to 24 carbon atoms, for example 2 to 20 carbon atoms, a polyoxyalkylene radical $-(R^4-O)_p-R^5$, or a polyiminoalkylene radical $-[R^6-N(R^7)]_q-(R^7)$, where $R^4$, $R^5$, $R^6$ and $R^7$ are each as defined above and q and p are each independently 1 to 50, and m is from 1 to 20 and preferably 2 to 10, for example three, four, five or six. The radicals of the formula IV preferably contain 1 to 50 and especially 2 to 20 nitrogen atoms.

In the case that $R^7$ is hydrogen, these amines, in a specific embodiment of the process according to the invention, can also be polyamidated or -imidated with the fatty acid (I).

In a specific embodiment, the process according to the invention is suitable for preparing fatty acid amides which bear tertiary amino groups and are thus basic, by reacting at least one fatty acid (I) with at least one polyamine bearing a primary and/or secondary and at least one tertiary amino group to give an ammonium salt and then converting the latter to the basic fatty acid amide under microwave irradiation in a reaction tube whose longitudinal axis is in the direction of propagation of the microwaves of a monomode microwave applicator. Tertiary amino groups are understood here to mean structural units in which one nitrogen atom does not bear acidic proton. For example, the nitrogen of the tertiary amino group may bear three hydrocarbon radicals or else be part of a heteroaromatic system. In this embodiment, $R^1$ preferably has one of the definitions given above, and is more preferably hydrogen, an aliphatic radical having 1 to 24 carbon atoms or an aryl group having 6 to 12 carbon atoms, and especially methyl, and $R^2$ is a hydrocarbon radical which bears tertiary amino groups and is of the formula V $$-(A)_s-Z \qquad (V)$$

in which

A is a divalent hydrocarbon radical having 2 to 50 carbon atoms, s is 0 or 1,

Z is a group of the formula $-NR^8R^9$ or a nitrogen-containing cyclic hydrocarbon radical having at least five ring members and $R^8$ and $R^9$ are each independently $C_1$- to $C_{20}$ hydrocarbon radicals, or polyoxyalkylene radicals of the formula (III).

A is preferably an alkylene radical having 2 to 24 carbon atoms, a cycloalkylene radical having 5 to 12 ring members, an arylene radical having 6 to 12 ring members or a heteroarylene radical having 5 to 12 ring members. A is more preferably an alkylene radical having 2 to 12 carbon atoms. s is preferably 1. More preferably, A is a linear or branched alkylene radical having 1 to 6 carbon atoms and s is 1.

A is additionally preferably, when Z is a group of the formula $-NR^8R^9$, a linear or branched alkylene radical having 2, 3 or 4 carbon atoms, especially an ethylene radical or a linear propylene radical. When Z, in contrast, is a nitrogen-containing cyclic hydrocarbon radical, particular preference is given to compounds in which A is a linear alkylene radical having 1, 2 or 3 carbon atoms, especially a methylene, ethylene or linear propylene radical.

Cyclical radicals preferred for the structural element A may be mono- or polycyclic and contain, for example, two or three ring systems. Preferred ring systems have 5, 6 or 7 ring members. They preferably contain a total of about 5 to 20 carbon atoms, especially 6 to 10 carbon atoms. Preferred ring systems are aromatic and contain only carbon atoms. In a specific embodiment, the structural elements A are formed from arylene radicals. The structural element A may bear substituents, for example alkyl radicals, halogen atoms, halogenated alkyl radicals, nitro, cyano and/or nitrile groups. When A is a monocyclic aromatic hydrocarbon, the amino groups or substituents bearing amino groups are preferably in ortho or para positions to one another.

Z is preferably a group of the formula $-NR^8R^9$. $R^8$ and $R^9$ therein are preferably each independently aliphatic, aromatic and/or araliphatic hydrocarbon radicals having 1 to 20 carbon atoms. Particularly preferred as $R^8$ and $R^9$ are alkyl radicals. When $R^8$ and/or $R^9$ are alkyl radicals, they preferably bear 1 to 14 carbon atoms, for example 1 to 6 carbon atoms. These alkyl radicals may be linear, branched and/or cyclic. $R^8$ and $R^9$ are more preferably each alkyl radicals having 1 to 4 carbon atoms, for example methyl, ethyl, n-propyl, isopropyl, n-butyl and isobutyl. In a further embodiment, the $R^8$ and/or $R^9$ radicals are each independently polyoxyalkylene radicals of the formula III.

Aromatic radicals particularly suitable as $R^8$ and/or $R^9$ include ring systems having at least 5 ring members. They may contain heteroatoms such as S, O and N. Araliphatic radicals particularly suitable as $R^8$ and/or $R^9$ include ring systems which have at least 5 ring members and are bonded to the nitrogen via a $C_1$-$C_6$ alkyl radical. They may contain heteroatoms such as S, O and N. The aromatic and also araliphatic radicals may bear further substituents, for example alkyl radicals, halogen atoms, halogenated alkyl radicals, nitro, cyano and/or nitrile groups.

In a further preferred embodiment, Z is a nitrogen-containing cyclic hydrocarbon radical whose nitrogen atom is not capable of forming amides. The cyclic system may be mono-, di- or else polycyclic. It preferably contains one or more five- and/or six-membered rings. This cyclic hydrocarbon may contain one or more, for example two or three, nitrogen atoms which do not bear acidic protons; it more preferably comprises one nitrogen atom. Particularly suitable are nitrogen containing aromatics whose nitrogen is involved in the formation of an aromatic π-electron sextet, for example pyridine. Likewise suitable are nitrogen-containing heteroaliphatics whose nitrogen atoms do not bear protons and whose valences are, for example, all satisfied with alkyl radicals. Z is joined to A or to the nitrogen of the formula (II) here preferably via a nitrogen atom of the heterocycle, as, for example, in the case of 1-(3-aminopropyl)pyrrolidine. The cyclic hydrocarbon represented by Z may bear further substituents, for example $C_1$-$C_{20}$-alkyl radicals, halogen atoms, halogenated alkyl radicals, nitro, cyano and/or nitrile groups.

In the case of inventive reactions of fatty acids with polyamines bearing at least one primary or secondary and at least one tertiary amino group, in spite of the presence of acids, no significant side reactions and more particularly no Hoffmann elimination of the tertiary amino group are observed.

According to the stoichiometric ratio between fatty acid (I) and polyamine (IV) or (V), one or more amino groups which each bear at least one hydrogen atom are converted to the fatty acid amide. In the reaction of polycarboxylic acids with polyamines of the formula IV, the primary amino groups in particular can also be converted to imides.

For the inventive preparation of primary amides, instead of ammonia, preference is given to using nitrogen compounds which eliminate ammonia gas when heated. Examples of such nitrogen compounds are urea and formamide.

Examples of suitable amines are ammonia, methylamine, ethylamine, propylamine, butylamine, hexylamine, cyclohexylamine, octylamine, decylamine, dodecylamine, tetradecylamine, hexadecylamine, octadecylamine, dimethylamine, diethylamine, ethylmethylamine, di-n-propylamine, diisopropylamine, dicyclohexylamine, didecylamine, didodecylamine, ditetradecylamine, dihexadecylamine, dioctadecylamine, benzylamine, phenylethylamine, ethylenediamine, diethylenetriamine, triethylenetetramine, tetraethylenepentamine and mixtures thereof. Examples of suitable amines bearing tertiary amino groups are N,N-dimethylethylenediamine, N,N-dimethyl-1,3-propanediamine, N,N-diethyl-1,3-propanediamine, N,N-dimethyl-2-methyl-1,3-propanediamine, 1-(3-aminopropyl)pyrrolidine, 1-(3-aminopropyl)-4-methylpiperazine, 3-(4-morpholino)-1-propylamine, 2-aminothiazole, the different isomers of N,N-dimethylaminoaniline, of aminopyridine, of aminomethylpyridine, of aminomethylpiperidine and of aminoquinoline, and also 2-aminopyrimidine, 3-aminopyrazole, aminopyrazine and 3-amino-1,2,4-triazole. Mixtures of different amines are also suitable. Among these, particular preference is given to dimethylamine, diethylamine, di-n-propylamine, diisopropylamine and ethylmethylamine.

The process is especially suitable for preparing N,N-dimethylhexanamide; N,N-dimethylcyclohexanamide, N-methyloctanamide, N,N-dimethyloctanamide, N,N-dimethyldecanamide, N-methylstearamide, N,N-dimethylstearamide, N-methylcocoamide, N,N-dimethylcocoamide, N-ethylcocoamide, N,N-diethylcocoamide, N,N-dimethyl tall oil fatty acid amide, N-octadecylhexanamide and N,N-dioctadecyloctanamide. It is additionally particularly suitable for preparing N-(N',N'-dimethylamino)propyldodecanamide, N-(N',N'-dimethylamino)propylcocoamide, N-(N',N'-dimethylamino)propyl tallow fatty acid amide, N-(N',N'-dimethylamino)ethylcocoamide, and N-(N',N'-dimethylamino)propyl palm fatty acid amide.

In the process according to the invention, fatty acid and amine can be reacted with one another in any desired ratios. The reaction between fatty acid and amine is preferably effected with molar ratios of 10:1 to 1:100, preferably of 2:1 to 1:10, especially of 1.2:1 to 1:3, based in each case on the molar equivalents of carboxyl and amino groups. In a specific embodiment, fatty acid and amine are used in equimolar amounts.

In many cases, it has been found to be advantageous to work with an excess of amine, i.e. molar ratios of amine to carboxyl groups of at least 1.01:1.00 and especially between 50:1 and 1.02:1, for example between 10:1 and 1.1:1. This converts the carboxyl groups virtually quantitatively to the amide. This process is particularly advantageous when the amine used is volatile. "Volatile" means here that the amine has a boiling point at standard pressure of preferably below 200° C., for example below 160° C., and can thus be removed by distillation from the amide.

The inventive preparation of the amides proceeds by reaction of fatty acid and amine to give the ammonium salt and subsequent irradiation of the salt with microwaves in a reaction tube whose longitudinal axis is in the direction of propagation of the microwaves in a monomode microwave applicator.

The salt is preferably irradiated with microwaves in a substantially microwave-transparent reaction tube within a hollow conductor connected to a microwave generator. The reaction tube is preferably aligned axially with the central axis of symmetry of the hollow conductor.

The hollow conductor which functions as the microwave applicator is preferably configured as a cavity resonator. Additionally preferably, the microwaves unabsorbed in the hollow conductor are reflected at the end thereof. Configuration of the microwave applicator as a resonator of the reflection type achieves a local increase in the electrical field strength at the same power supplied by the generator and increased energy exploitation.

The cavity resonator is preferably operated in $E_{01n}$ mode where n is an integer and specifies the number of field maxima of the microwave along the central axis of symmetry of the resonator. In this operation, the electrical field is directed in the direction of the central axis of symmetry of the cavity resonator. It has a maximum in the region of the central axis of symmetry and decreases to the value 0 toward the outer surface. This field configuration is rotationally symmetric about the central axis of symmetry. According to the desired flow rate of the reaction mixture through the reaction tube, the temperature required and the residence time required in the resonator, the length of the resonator is selected relative to the wavelength of the microwave radiation used. n is preferably an integer from 1 to 200, more preferably from 2 to 100, particularly from 4 to 50 and especially from 3 to 20, for example 3, 4, 5, 6, 7 or 8.

The microwave energy can be injected into the hollow conductor which functions as the microwave applicator through holes or slots of suitable dimensions. In an embodiment particularly preferred in accordance with the invention, the ammonium salt is irradiated with microwaves in a reaction tube present in a hollow conductor with a coaxial transition of the microwaves. Microwave devices particularly preferred from this process are formed from a cavity resonator, a coupling device for injecting a microwave field into the cavity resonator and with one orifice each on two opposite end walls for passage of the reaction tube through the resonator. The microwaves are preferably injected into the cavity resonator by means of a coupling pin which projects into the cavity resonator. The coupling pin is preferably configured as a preferably metallic inner conductor tube which functions as a coupling antenna. In a particularly preferred embodiment, this coupling pin projects through one of the end orifices into the cavity resonator. The reaction tube more preferably adjoins the inner conductor tube of the coaxial transition, and is especially conducted through the cavity thereof into the cavity resonator. The reaction tube is preferably aligned axially with a central axis of symmetry of the cavity resonator, for which the cavity resonator preferably has one central orifice each on two opposite end walls for passage of the reaction tube.

The microwaves can be fed into the coupling pin or into the inner conductor tube which functions as a coupling antenna, for example, by means of a coaxial connecting line. In a preferred embodiment, the microwave field is supplied to the resonator via a hollow conductor, in which case the end of the coupling pin projecting out of the cavity resonator is conducted into the hollow conductor through an orifice in the wall of the hollow conductor, and takes microwave energy from the hollow conductor and injects it into the resonator. In a specific embodiment, the salt is irradiated with microwaves in a microwave-transparent reaction tube which is axially symmetric within an $E_{01n}$ round hollow conductor with a coaxial transition of the microwaves. In this case, the reaction tube is conducted through the cavity of an inner conductor tube which functions as a coupling antenna into the cavity resonator. In a further preferred embodiment, the salt is irradiated with microwaves in a microwave-transparent reaction tube which is conducted through an $E_{01n}$ cavity resonator with axial feeding of the microwaves, the length of the cavity resonator being such that n=2 or more field maxima of the microwave form. In a further preferred embodiment, the salt is irradiated with microwaves in a microwave-transparent reaction tube which is axially symmetric within a circular cylindrical $E_{01n}$ cavity resonator with a coaxial transition of the microwaves, the length of the cavity resonator being such that n=2 or more field maxima of the microwave form.

Microwave generators, for example the magnetron, the klystron and the gyrotron, are known to those skilled in the art.

The reaction tubes used to perform the process according to the invention are preferably manufactured from substantially microwave-transparent, high-melting material. Particular preference is given to using nonmetallic reaction tubes. "Substantially microwave-transparent" is understood here to mean materials which absorb a minimum amount of microwave energy and convert it to heat. A measure employed for the ability of a substance to absorb microwave energy and convert it to heat is often the dielectric loss factor tan $\delta=\in''/\in'$. The dielectric loss factor tan $\delta$ is defined as the ratio of dielectric loss $\in''$ to dielectric constant C. Examples of tan $\delta$ values of different materials are reproduced, for example, in D. Bogdal, Microwave-assisted Organic Synthesis, Elsevier 2005. For reaction tubes suitable in accordance with the invention, materials with tan $\delta$ values measured at 2.45 GHz and 25° C. of less than 0.01, particularly less than 0.005 and especially less than 0.001 are preferred. Preferred microwave-transparent and thermally stable materials include primarily mineral-based materials, for example quartz, aluminum oxide, zirconium oxide and the like. Other suitable tube materials are thermally stable plastics, such as especially fluoropolymers, for example Teflon, and industrial plastics such as polypropylene, or polyaryl ether ketones, for example glass fiber-reinforced polyetheretherketone (PEEK). In order to withstand the temperature conditions during the reaction, minerals, such as quartz or aluminum oxide, coated with these plastics have been found to be especially suitable as reactor materials.

Reaction tubes particularly suitable for the process according to the invention have an internal diameter of 1 mm to approx. 50 cm, especially between 2 mm and 35 cm for example between 5 mm and 15 cm. Reaction tubes are understood here to mean vessels whose ratio of length to diameter is greater than 5, preferably between 10 and 100 000, more preferably between 20 and 10 000, for example between 30 and 1000. A length of the reaction tube is understood here to mean the length of the reaction tube over which the microwave irradiation proceeds. Baffles and/or other mixing elements can be incorporated into the reaction tube.

$E_{01}$ cavity resonators particularly suitable for the process according to the invention preferably have a diameter which corresponds to at least half the wavelength of the microwave radiation used. The diameter of the cavity resonator is preferably 1.0 to 10 times, more preferably 1.1 to 5 times and especially 2.1 to 2.6 times half the wavelength of the microwave radiation used. The $E_{01}$ cavity resonator preferably has a round cross section, which is also referred to as an $E_{01}$ round hollow conductor. It more preferably has a cylindrical shape and especially a circular cylindrical shape.

The reaction tube is typically provided at the inlet with a metering pump and a manometer, and at the outlet with a pressure-retaining device and a heat exchanger. This makes possible reactions within a very wide pressure and temperature range.

The conversion of amine and fatty acid to the ammonium salt can be performed continuously, batchwise or else in semi-batchwise processes. Thus, the preparation of the ammonium salt can be performed in an upstream (semi-)batchwise process, for example in a stirred vessel. The ammonium salt is preferably obtained in situ and not isolated. In a preferred embodiment, the amine and fatty acid reactants, each independently optionally diluted with solvent, are only mixed shortly before entry into the reaction tube. For instance, it has been found to be particularly useful to undertake the reaction of amine and fatty acid to give the ammonium salt in a mixing zone, from which the ammonium salt, optionally after intermediate cooling, is conveyed into the reaction tube. Additionally preferably, the reactants are supplied to the process according to the invention in liquid form. For this purpose, it is possible to use relatively high-melting and/or relatively high-viscosity reactants, for example in the molten state and/or admixed with solvent, for example in the form of a solution, dispersion or emulsion. A catalyst can, if used, be added to one of the reactants or else to the reactant mixture before entry into the reaction tube. It is also possible to convert solid, pulverulent and heterogeneous systems by the process according to the invention, in which case merely appropriate industrial apparatus for conveying the reaction mixture is required.

The ammonium salt can be fed into the reaction tube either at the end conducted through the inner conductor tube or at the opposite end.

By variation of tube cross section, length of the irradiation zone (this is understood to mean the length of the reaction tube in which the reaction mixture is exposed to microwave radiation), flow rate, geometry of the cavity resonator, the microwave power injected and the temperature achieved, the reaction conditions are established such that the maximum reaction temperature is attained as rapidly as possible and the residence time at maximum temperature remains sufficiently short that as low as possible a level of side reactions or further reactions occurs. To complete the reaction, the reaction mixture can pass through the reaction tube more than once, optionally after intermediate cooling. In many cases, it has been found to be useful when the reaction product is cooled immediately after leaving the reaction tube, for example by jacket cooling or decompression. In the case of slower reactions, it has often been found to be useful to keep the reaction product at reaction temperature for a certain time after it leaves the reaction tube.

The advantages of the process according to the invention lie in very homogeneous irradiation of the reaction mixture in the center of a symmetric microwave field within a reaction tube, the longitudinal axis of which is in the direction of propagation of the microwaves of a monomode microwave applicator and especially within an $E_{01}$ cavity resonator, for example with a coaxial transition. The inventive reactor design allows the performance of reactions also at very high pressures and/or temperatures. By increasing the temperature and/or pressure, a significant rise in the degree of conversion and yield is observed even compared to known microwave reactors, without this resulting in undesired side reactions and/or discoloration. Surprisingly, this achieves a very high efficiency in the exploitation of the microwave energy injected into the cavity resonator, which is typically more than 50%, often more than 80%, in some cases more than 90% and in special cases more than 95%, for example more than 98%, of the microwave power injected, and therefore gives economic and also ecological advantages over conventional preparation processes, and also over prior art microwave processes.

The process according to the invention additionally allows a controlled, safe and reproducible reaction regime. Since the reaction mixture in the reaction tube is moved parallel to the direction of propagation of the microwaves, known overheating phenomena as a result of uncontrolled field distributions, which lead to local overheating as a result of changing intensities of the field, for example in wave crests and nodes, are balanced out by the flowing motion of the reaction mixture. The advantages mentioned also allow working with high microwave powers of, for example, more than 10 kW or more than 100 kW and thus, in combination with only a short residence time in the cavity resonator, accomplishment of large production amounts of 100 or more tonnes per year in one plant.

It was particularly surprising that, in spite of the only very short residence time of the ammonium salt in the microwave field in the flow tube with continuous flow, very substantial amidation takes place with conversions generally of more than 80%, often even more than 90%, for example more than 95%, based on the component used in deficiency, without significant formation of by-products. In the case of a corresponding conversion of these ammonium salts in a flow tube, of the same dimensions with thermal jacket heating, achievement of suitable reaction temperatures requires extremely high wall temperatures which lead to formation of undefined polymers and colored species, but only minor amide formation in the same time interval. In addition, the products prepared by the process according to the invention have very low metal contents, without requiring a further workup of the crude products. For instance, the metal contents of the products prepared by the process according to the invention, based on iron as the main element, are typically less than 25 ppm, preferably less than 15 ppm, especially less than 10 ppm, for example between 0.01 and 5 ppm, of iron.

The temperature rise caused by the microwave radiation is preferably limited to a maximum of 500° C., for example, by regulating the microwave intensity of the flow rate and/or by cooling the reaction tube, for example by means of a nitrogen stream. It has been found to be particularly useful to perform the reaction at temperatures between 150 and a maximum of 400° C. and especially between 180 and a maximum of 300° C., for example at temperatures between 200 and 270° C.

The duration of the microwave irradiation depends on various factors, for example the geometry of the reaction tube, the microwave energy injected, the specific reaction and the desired degree of conversion. Typically, the microwave irradiation is undertaken over a period of less than 30 minutes, preferably between 0.01 second and 15 minutes, more preferably between 0.1 second and 10 minutes and especially between 1 second and 5 minutes, for example between 5 seconds and 2 minutes. The intensity (power) of the microwave radiation is adjusted such that the reaction mixture has the desired maximum temperature when it leaves the cavity resonator. In a preferred embodiment, the reaction product, directly after the microwave irradiation has ended, is cooled as rapidly as possible to temperatures below 120° C., preferably below 100° C. and especially below 60° C.

The reaction is preferably performed at pressures between 0.01 and 500 bar and more preferably between 1 bar (atmospheric pressure) and 150 bar and especially between 1.5 bar and 100 bar, for example between 3 bar and 50 bar. It has been found to be particularly useful to work under elevated pressure, which involves working above the boiling point (at standard pressure) of the reactants or products, or of any solvent present, and/or above the water of reaction formed during the reaction. The pressure is more preferably adjusted to a sufficiently high level that the reaction mixture remains in the liquid state during the microwave irradiation and does not boil.

To avoid side reactions and to prepare products of maximum purity, it has been found to be useful to handle reactants and products in the presence of an inert protective gas, for example nitrogen, argon or helium.

In a preferred embodiment, the reaction is accelerated or completed by working in the presence of dehydrating catalysts. Preference is given to working in the presence of an acidic inorganic, organometallic or organic catalyst, or mixtures of two or more of these catalysts.

Acidic inorganic catalysts in the context of the present invention include, for example, sulfuric acid, phosphoric acid, phosphonic acid, hypophosphorous acid, aluminum sulfide hydrate, alum, acidic silica gel and acidic aluminum hydroxide. In addition, for example, aluminum compounds of the general formula $Al(OR^{15})_3$ and titanates of the general formula $Ti(OR^{15})_4$ are usable as acidic inorganic catalysts, where $R^{15}$ radicals may each be the same or different and are each independently selected from $C_1$-$C_{10}$ alkyl radicals, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, sec-hexyl, n-heptyl, n-octyl, 2-ethylhexyl, n-nonyl or n-decyl, $C_3$-$C_{12}$ cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. The $R^{15}$ radicals in $Al(OR^{15})_3$ or $Ti(OR^{15})_4$ are preferably each the same and are selected from isopropyl, butyl and 2-ethylhexyl.

Preferred acidic organometallic catalysts are, for example, selected from dialkyltin oxides $(R^{15})_2SnO$, where $R^{15}$ is as defined above. A particularly preferred representative of acidic organometallic catalysts is di-n-butyltin oxide, which is commercially available as "Oxo-tin" or as Fascat® brands.

Preferred acidic organic catalysts are acidic organic compounds with, for example, phosphate groups, sulfo groups, sulfate groups or phosphonic acid groups. Particularly preferred sulfonic acids contain at least one sulfo group and at least one saturated or unsaturated, linear, branched and/or cyclic hydrocarbon radical having 1 to 40 carbon atoms and preferably having 3 to 24 carbon atoms. Especially preferred are aromatic sulfonic acids, especially alkylaromatic monosulfonic acids having one or more $C_1$-$C_{28}$ alkyl radicals and especially those having $C_3$-$C_{22}$ alkyl radicals. Suitable examples are methanesulfonic acid, butanesulfonic acid, benzenesulfonic acid, p-toluenesulfonic acid, xylenesulfonic acid, 2-mesitylenesulfonic acid, 4-ethylbenzenesulfonic acid, isopropylbenzenesulfonic acid, 4-butylbenzenesulfonic acid, 4-octylbenzenesulfonic acid; dodecylbenzenesulfonic acid, didodecylbenzenesulfonic acid, naphthalenesulfonic acid. It is also possible to use acidic ion exchangers as acidic organic catalysts, for example sulfo-containing poly(styrene) resins crosslinked with about 2 mol % of divinylbenzene.

Particular preference for the performance of the process according to the invention is given to boric acid, phosphoric acid, polyphosphoric acid and polystyrenesulfonic acids. Especially preferred are titanates of the general formula $Ti(OR^{15})_4$, and especially titanium tetrabutoxide and titanium tetraisopropoxide.

If the use of acidic inorganic, organometallic or organic catalysts is desired, in accordance with the invention, 0.01 to 10% by weight, preferably 0.02 to 2% by weight, of catalyst is used. In a particularly preferred embodiment, no catalyst is employed.

In a further preferred embodiment, the microwave irradiation is performed in the presence of acidic solid catalysts. This involves suspending the solid catalyst in the ammonium salt optionally admixed with solvent, or advantageously passing the ammonium salt optionally admixed with solvent over a fixed bed catalyst and exposing it to microwave radiation. Suitable solid catalysts are, for example, zeolites, silica gel, montmorillonite and (partly) crosslinked polystyrenesulfonic acid, which may optionally be integrated with catalytically active metal salts. Suitable acidic ion exchangers based on polystyrenesulfonic acids, which can be used as solid phase catalysts, are obtainable, for example, from Rohm & Haas under the Amberlyst® brand name.

It has been found to be useful to work in the presence of solvents in order, for example, to lower the viscosity of the reaction medium and/or to fluidize the reaction mixture if it is heterogeneous. For this purpose, it is possible in principle to use all solvents which are inert under the reaction conditions employed and do not react with the reactants or the products formed. An important factor in the selection of suitable solvents is the polarity thereof, which firstly determines the dissolution properties and secondly the degree of interaction with microwave radiation. A particularly important factor in the selection of suitable solvents is the dielectric loss $\in''$ thereof. The dielectric loss $\in''$ describes the proportion of microwave radiation which is converted to heat in the interaction of a substance with microwave radiation. The latter value has been found to be a particularly important criterion for the suitability of a solvent for the performance of the process according to the invention. It has been found to be particularly useful to work in solvents which exhibit minimum microwave absorption and hence make only a small contribution to the heating of the reaction system. Solvents preferred for the process according to the invention have a dielectric loss $\in''$ measured at room temperature and 2450 MHz of less than 10 and preferably less than 1, for example less than 0.5. An overview of the dielectric loss of different solvents can be found, for example, in "Microwave Synthesis" by B. L. Hayes, CEM Publishing 2002. Suitable solvents for the process according to the invention are especially those with $\in''$ values less than 10, such as N-methylpyrrolidone, N,N-dimethylformamide or acetone, and especially solvents with $\in''$ values less than 1. Examples of particularly preferred solvents with $\in''$ values less than 1 are aromatic and/or aliphatic hydrocarbons, for example toluene, xylene, ethylbenzene, tetralin, hexane, cyclohexane, decane, pentadecane, decalin, and also commercial hydrocarbon mixtures, such as benzine fractions, kerosene, Solvent Naphtha, ®Shellsol AB, ®Solvesso 150, ®Solvesso 200, ®Exxsol, ®Isopar and ®Shellsol products. Solvent mixtures which have $\in''$ values preferably below 10 and especially below 1 are equally preferred for the performance of the process according to the invention.

In principle, the process according to the invention is also performable in solvents with higher ∈" values of, for example, 5 or higher, such as especially with ∈" values of 10 or higher. However, the accelerated heating of the reaction mixture observed requires special measures to comply with the maximum temperature.

When working in the presence of solvents, the proportion thereof in the reaction mixture is preferably between 2 and 95% by weight, especially between 5 and 90% by weight and particularly between 10 and 75% by weight, for example between 30 and 60% by weight. Particular preference is given to performing the reaction without solvents.

Microwaves refer to electromagnetic rays with a wavelength between about 1 cm and 1 m, and frequencies between about 300 MHz and 30 GHz. This frequency range is suitable in principle for the process according to the invention. For the process according to the invention, preference is given to using microwave radiation with the frequencies approved for industrial, scientific and medical applications, for example with frequencies of 915 MHz, 2.45 GHz, 5.8 GHz or 27.12 GHz.

The microwave power to be injected into the cavity resonator for the performance of the process according to the invention is especially dependent on the geometry of the reaction tube and hence of the reaction volume, and on the duration of the irradiation required. It is typically between 200 W and several hundred kW and especially between 500 W and 100 kW for example between 1 kW and 70 kW. It can be generated by means of one or more microwave generators.

In a preferred embodiment, the reaction is performed in a pressure-resistant inert tube, in which case the water of reaction which forms and possibly reactants and, if present, solvent lead to a pressure buildup. After the reaction has ended, the elevated pressure can be used by decompression for volatilization and removal of water of reaction, excess reactants and any solvent and/or to cool the reaction product. In a further embodiment, the water of reaction formed, after cooling and/or decompression, is removed by customary processes, for example phase separation, distillation, stripping, flashing and/or absorption.

To complete the conversion, it has in many cases been found to be useful to expose the crude product obtained, after removal of water of reaction and if appropriate discharge of product and/or by-product, again to microwave irradiation, in which case the ratio of the reactants used may have to be supplemented to replace consumed or deficient reactants.

The process according to the invention allows a very rapid, energy-saving and inexpensive preparation of fatty acid amides in high yields and with high purity in industrial scale amounts. The very homogeneous irradiation of the ammonium salt in the center of the rotationally symmetric microwave field allows a safe, controllable and reproducible reaction regime. At the same time, a very high efficiency in the exploitation of the incident microwave energy achieves an economic viability distinctly superior to the known preparation processes. In this process, no significant amounts of by-products are obtained. Such rapid and selective reactions cannot be achieved by conventional methods and were not to be expected solely through heating to high temperatures. In addition, fatty acid amides prepared by the inventive route are typically obtained in a purity sufficient for further use, such that no further workup or further processing steps are required. For specific applications, they can, however, be purified further by customary purification processes, for example distillation, recrystallization, filtration or chromatographic processes.

EXAMPLES

The conversions of the ammonium salts under microwave irradiation were effected in a ceramic tube (60×1 cm) which was present in axial symmetry in a cylindrical cavity resonator (60×10 cm). On one of the end sides of the cavity resonator, the ceramic tube passed through the cavity of an inner conductor tube which functions as a coupling antenna. The microwave field with a frequency of 2.45 GHz, generated by a magnetron, was injected into the cavity resonator by means of the coupling antenna ($E_{01}$ cavity applicator; monomode).

The microwave power was in each case adjusted over the experiment time in such a way that the desired temperature of the reaction mixture at the end of the irradiation zone was kept constant. The microwave powers mentioned in the experiment descriptions therefore represent the mean value of the microwave power injected over time. The measurement of the temperature of the reaction mixture was undertaken directly after it had left the reaction zone (distance about 15 cm in an insulated stainless steel capillary, Ø 1 cm) by means of a Pt100 temperature sensor. Microwave energy not absorbed directly by the reaction mixture was reflected at the end side of the cavity resonator at the opposite end to the coupling antenna; the microwave energy which was also not absorbed by the reaction mixture on the return path and reflected back in the direction of the magnetron was passed with the aid of a prism system (circulator) into a water-containing vessel. The difference between energy injected and heating of this water load was used to calculate the microwave energy introduced into the reaction mixture.

By means of a high-pressure pump and of a suitable pressure-release valve, the reaction mixture in the reaction tube was placed under such a working pressure which was sufficient always to keep all reactants and products or condensation products in the liquid state. The reaction mixtures prepared from fatty acid and amine were pumped with a constant flow rate through the reaction tube, and the residence time in the irradiation zone was adjusted by modifying the flow rate.

The products were analyzed by means of $^1$H NMR spectroscopy at 500 MHz in $CDCl_3$. The properties were determined by means of atomic absorption spectroscopy.

Example 1

Preparation of N,N-dimethylcocoamide

While cooling with dry ice, 0.72 kg of dimethylamine (16 mol) from a reservoir bottle was condensed into a cold trap. A 10 l Büchi stirred autoclave with gas inlet tube, stirrer, internal thermometer and pressure equalizer was initially charged with 3.5 kg of cyclohexane and 3.1 kg of coconut fatty acid (15 mol), which were heated to 60° C. until the mixture became homogeneous. By slowly thawing the cold trap, gaseous dimethylamine was passed through the gas inlet tube into the stirred autoclave. In a strongly exothermic reaction, the coconut fatty acid N,N-dimethylammonium salt formed.

The mixture thus obtained was pumped through the reaction tube continuously at 6.0 l/h at a working pressure of 40 bar and exposed to a microwave power of 2.9 kW, 95% of which was absorbed by the reaction mixture. The residence time of the reaction mixture in the irradiation zone was approx. 29 seconds. At the end of the reaction tube, the reaction mixture had a temperature of 277° C.

A conversion of 95% of theory was attained. The reaction product was slightly yellowish in color and contained<2 ppm of iron. After distillative removal of cyclohexane, water of reaction and excess amine, 3.7 kg of N,N-dimethylcocoamide were obtained with a purity of 95%.

Example 2

Preparation of N-ethylacetamide

While cooling with ice, 1.8 kg of ethylamine (40 mol) were introduced by means of a dropping funnel into a solution consisting of 3.5 kg of cyclohexane and 2.4 kg of acetic acid (40 mol) in a 10 l Büchi stirred autoclave with gas inlet tube, stirrer, internal thermometer and pressure equalizer. In a strongly exothermic reaction, the N-ethylammonium acetate formed.

The ammonium salt thus obtained was pumped through the reaction tube continuously at 6.0 l/h at a working pressure of 25 bar and exposed to a microwave power of 2.5 kW, 91% of which was absorbed by the reaction mixture. The residence time of the reaction mixture in the irradiation zone was approx. 29 seconds. At the end of the reaction tube, the reaction mixture had a temperature of 267° C.

A conversion of 92% of theory was attained. The reaction product was slightly yellowish in color and contained<2 ppm of iron. After distillative removal of cyclohexane and water of reaction, 2.3 kg of N-ethylacetamide were obtained with a purity of 94%.

Example 3

Preparation of N,N-dimethylcocoamide in an Autoclave

Comparative Example

A 1 litre stirred autoclave was initially charged with 500 ml of reaction solution (for sample preparation see example 1), which were heated to 270° C. in a closed apparatus with maximum heating output with vigorous stirring within 8 minutes (oil feed temperature 350° C.). The reaction mixture was stirred further under pressure for 5 minutes and then cooled to room temperature by means of cold oil circulation.

The reaction mixture thus treated exhibited a conversion of only 45% of the theoretically possible yield. The crude product contained 45 ppm of iron. In addition, as well as black caking in the autoclave, pyrolysis products were also found in the product itself, recognizable as finely dispersed solids. The product was characterized by a dark orange color and a distinct burnt odor.

Example 4

Preparation of N,N-dimethylcocoamide in a Heat Exchanger at Elevated Temperature/Pressure

Comparative Experiment

While cooling with dry ice, 0.72 kg of dimethylamine (16 mol) from a reservoir bottle were condensed into a cold trap. A 10 l Büchi stirred autoclave with gas inlet tube, stirrer, internal thermometer and pressure equalizer was initially charged with 3.5 kg of toluene and 3.1 kg of coconut fatty acid (15 mol), which were heated to 60° C. until the mixture became homogeneous. By slowly thawing the cold trap, gaseous dimethylamine was passed through the gas inlet tube into the stirred autoclave. In a strongly exothermic reaction, the coconut fatty acid N,N-dimethylammonium salt formed. Subsequently, the product was conveyed through a very effective heat exchanger (microreactor; channel diameter 1 mm) in such a way that a residence time of 1.5 minutes at a temperature of 275° C. measured by means of PT100 was achieved. The total delivery output was 5 liters/h.

A conversion of 69% of theory was attained. The reaction product was brownish-black in color (iodine color number>10), contained 75 ppm of iron and had a distinct burnt odor.

Example 5

Preparation of N-(3-N,N-dimethylamino)propyl)octylamide

A 10 l Büchi stirred autoclave with gas inlet tube, stirrer, internal thermometer and pressure equalizer was initially charged with 2.89 kg of caprylic acid (20 mol) which were heated to 45° C. At this temperature, 2.04 kg of dimethylaminopropylamine (20 mol) were slowly added while cooling. In an exothermic reaction, the caprylic acid (N',N'-dimethylaminopropyl)ammonium salt formed.

The ammonium salt thus obtained was pumped continuously through the reaction tube at 5.6 l/h at a working pressure of 35 bar and exposed to a microwave power of 3.1 kW, 92% of which was absorbed by the reaction mixture. The residence time of the reaction mixture in the irradiation zone was approx. 30 seconds. At the end of the reaction tube, the reaction mixture had a temperature of 280° C.

A conversion of approx. 93% of theory was attained. The reaction product was slightly yellowish and contained<2 ppm of iron. After distillative removal of the water of reaction, 4.7 kg of caprylic acid (N',N'-dimethylaminopropyl)amide were obtained with a purity of 94%.

Example 6

Preparation of N,N-dimethyloleamide

While cooling with dry ice, 0.9 kg of dimethylamine (20 mol) from a reservoir bottle was condensed into a cold trap. A 10 l Büchi stirred autoclave with gas inlet tube, stirrer, internal thermometer and pressure equalizer was initially charged with 3.5 kg of cyclohexane and 5.65 kg of technical-grade oleic acid (20 mol), which were heated to 60° C. until the mixture became homogeneous. By slowly thawing the cold trap, gaseous dimethylamine was passed through the gas inlet tube into the stirred autoclave. In a strongly exothermic reaction, the oleic acid N,N-dimethylammonium salt formed.

The mixture thus obtained was pumped continuously through the reaction tube at 5.6 l/h at a working pressure of 35 bar and exposed to a microwave power of 3.1 kW, 92% of which was absorbed by the reaction mixture. The residence time of the reaction mixture in the irradiation zone was approx. 30 seconds. At the end of the reaction tube, the reaction mixture had a temperature of 280° C.

A conversion of 94% of theory was attained. The reaction product was slightly yellowish and contained<2 ppm of iron. After distillative removal of water of reaction and cyclohexane, 6.35 kg of N—N-dimethyloleamide were obtained with a purity of 95%.

The invention claimed is:
1. A continuous process for preparing a fatty acid amide comprising the steps of reacting at least one fatty acid of the formula I

$$R^3\text{—COOH} \qquad (I)$$

wherein $R^3$ is a substituted or unsubstituted aliphatic hydrocarbon radical having 5 to 50 carbon atoms with at least one amine of the formula II $$HNR^1R^2 \quad (II)$$

wherein $R^1$ and $R^2$ are each independently hydrogen or a hydrocarbon radical having 1 to 100 carbon atoms forming an ammonium salt and subsequently converting this ammonium salt to the fatty acid amide under microwave irradiation in a reaction tube whose longitudinal axis is in the direction of propagation of the microwaves from a monomode microwave applicator and whose ratio of length to diameter is greater than 5, wherein the microwave applicator is configured as a cavity resonator, and wherein the cavity resonator is operated in $E_{01n}$ mode where n is an integer from 1 to 200.

2. The process as claimed in claim 1, wherein the salt is irradiated with microwaves in a substantially microwave-transparent reaction tube within a hollow conductor connected via waveguides to a microwave generator.

3. The process as claimed in claim 1, wherein the microwave applicator is configured as a cavity resonator of the reflection type.

4. The process as claimed in claim 1, wherein the reaction tube is aligned axially with a central axis of symmetry of the hollow conductor.

5. The process as claimed in claim 1, wherein the salt is irradiated in a cavity resonator with a coaxial transition of the microwaves.

6. The process as claimed in claim 1, wherein the cavity resonator is operated in $E_{01n}$ mode where n is an integer from 4 to 50.

7. The process as claimed in claim 1, wherein $R^3$ is an unsubstituted alkyl radical having 5 to 50 carbon atoms.

8. The process as claimed in claim 1, wherein $R^3$ is a hydrocarbon radical which has 5 to 50 carbon atoms and at least one substituent selected from the group consisting of halogen atoms, $C_1$-$C_5$-alkoxyalkyl, poly($C_1$-$C_5$-alkoxy)alkyl, carboxyl, ester, amide, cyano, nitrile, nitro, sulfo and aryl groups having 5 to 20 carbon atoms, where the $C_5$-$C_{20}$-aryl groups may have substituents selected from the group consisting of halogen atoms, halogenated alkyl radicals, $C_1$-$C_{20}$-alkyl, $C_2$-$C_{20}$-alkenyl, $C_1$-$C_5$-alkoxy, ester, amide, cyano, nitrile and nitro groups.

9. The process as claimed in claim 1, wherein $R^3$ comprises 5 to 30 carbon atoms.

10. The process as claimed in claim 1, wherein $R^3$ comprises one or more double bonds.

11. The process as claimed in claim 1, wherein $R^1$ and $R^2$ are each independently a hydrocarbon radical having 1 to 100 carbon atoms.

12. The process as claimed in claim 1, wherein $R^1$ is a hydrocarbon radical having 1 to 100 carbon atoms and $R^2$ is hydrogen.

13. The process as claimed in claim 1, wherein $R^1$ or $R^2$ or both have substituents selected from the group consisting of $C_1$-$C_5$-alkoxyalkyl, cyano, nitrile, nitro and $C_5$-$C_{20}$-aryl groups.

14. The process as claimed in claim 1, wherein $R^1$ or $R^2$ or both are substituted by $C_5$-$C_{20}$-aryl groups, wherein the $C_5$-$C_{20}$-aryl groups have at least one substituent selected from the group consisting of halogen atoms, halogenated alkyl radicals, $C_1$-$C_{20}$-alkyl, $C_2$-$C_{20}$-alkenyl, $C_1$-$C_5$-alkoxy, ester, amide, cyano, nitrile and nitro-substituted phenyl radicals.

15. The process as claimed in claim 1, wherein $R^1$ and $R^2$ together with the nitrogen atom to which they are bonded form a ring.

16. The process as claimed in claim 1, wherein $R^1$ and $R^2$ are each independently a radical of the formula III $$-(R^4-O)_n-R^5 \quad (III)$$

wherein
$R^4$ is an alkylene group having 2 to 6 carbon atoms,
$R^5$ is a hydrocarbon radical having 1 to 24 carbon atoms or a group of the formula $-NR^{10}R^{11}$,
n is an integer from 2 to 50 and
$R^{10}$, $R^{11}$ are each independently an aliphatic radical having 1 to 24 carbon atoms, an aryl group or heteroaryl group having 5 to 12 ring members, a poly(oxyalkylene) group having 1 to 50 poly(oxyalkylene) units, where the poly(oxyalkylene) units derive from alkylene oxide units having 2 to 6 carbon atoms, or $R^{10}$ and $R^{11}$ together with the nitrogen atom to which they are bonded form a ring having 4, 5, 6 or more ring members.

17. The process as claimed in claim 1, wherein $R^1$ and $R^2$ are each independently a radical of the formula IV $$-[R^6-N(R^7)]_m-(R^7) \quad (IV)$$

wherein
$R^6$ is an alkylene group having 2 to 6 carbon atoms or mixtures thereof,
each $R^7$ is independently hydrogen, an alkyl radical having up to 24 carbon atoms, a polyoxyalkylene radical $-(R^4-O)_p-R^5$, or a polyiminoalkylene radical $-[R^6-N(R^7)]_q-(R^7)$, where $R^4$, $R^5$, $R^6$ and $R^7$ are each as defined above and q and p are each independently 1 to 50, and
m is from 1 to 20.

18. The process as claimed in claim 1, wherein the microwave irradiation is performed at temperatures between 150 and 300° C.

19. The process as claimed in claim 1, wherein the microwave irradiation is performed at pressures above atmospheric pressure.

20. The process as claimed in claim 1, wherein $R^1$ or $R^2$ or both substituents are independently an aliphatic radical having 1 to 24 carbon atoms.

21. The process as claimed in claim 16, wherein $R^{10}$ and $R^{11}$ are each independently an aliphatic radical having 2 to 18 carbon atoms.

22. The process as claimed in claim 17, wherein m is from 2 to 10.

* * * * *